United States Patent
Haffner (10) Patent No.: US 8,825,214 B2
(45) Date of Patent: Sep. 2, 2014

(54) METHOD OF ANALYZING AND CONTROLLING A COMBUSTION PROCESS IN A GAS TURBINE AND APPARATUS FOR PERFORMING THE METHOD

(75) Inventor: Ken Yves Haffner, Baden (CH)

(73) Assignee: Alstom Technology Ltd., Baden (CH)

( * ) Notice: Subject to any disclaimer, the term of this patent is extended or adjusted under 35 U.S.C. 154(b) by 66 days.

(21) Appl. No.: 13/300,110

(22) Filed: Nov. 18, 2011

(65) Prior Publication Data

US 2012/0136483 A1    May 31, 2012

(30) Foreign Application Priority Data

Nov. 30, 2010    (EP) .................................... 10193189

(51) Int. Cl.
*G01B 21/02* (2006.01)
*G01J 5/00* (2006.01)
*G01N 21/27* (2006.01)
*G01J 3/42* (2006.01)
*G01N 21/35* (2014.01)
*G01N 21/39* (2006.01)
*G01J 3/28* (2006.01)
*G01J 5/08* (2006.01)

(52) U.S. Cl.
CPC ........ *G01J 5/0014* (2013.01); *G01J 2003/2833* (2013.01); *G01N 21/274* (2013.01); *G01J 3/42* (2013.01); *G01J 2003/423* (2013.01); *G01N 21/3504* (2013.01); *G01J 2003/2873* (2013.01); *G01J 5/0821* (2013.01); *G01N 21/39* (2013.01)
USPC ............... 700/274; 701/100; 702/23; 702/24; 702/27; 702/30; 702/31; 702/32; 700/266; 422/82.07; 422/82.08; 422/83; 422/94; 60/239; 60/39.34; 60/735; 60/805; 60/349

(58) Field of Classification Search
CPC ......... G01J 3/42; G01J 5/0014; G01J 5/0821; G01J 2003/2833; G01J 2003/2873; G01J 2003/423; G01N 21/274; G01N 21/3504; G01N 21/39
USPC ............ 60/239, 39.94, 735, 805, 349, 39.34; 422/82.07, 82.08, 83, 94; 700/266, 700/287; 702/FOR. 113, FOR. 114, 23, 24, 702/27, 30–32; 701/100
See application file for complete search history.

(56) References Cited

U.S. PATENT DOCUMENTS

| 6,271,522 B1 | 8/2001 | Lindermeir et al. |
| 2004/0118348 A1* | 6/2004 | Mills ..................... 118/723 MW |

(Continued)

FOREIGN PATENT DOCUMENTS

| DE | 19821956 A1 | 11/1999 |
| DE | 102008010229 B3 | 7/2009 |

(Continued)

*Primary Examiner* — Shogo Sasaki
(74) *Attorney, Agent, or Firm* — Buchanan Ingersoll & Rooney PC (57) ABSTRACT

A method is provided for the measurement of parameters of a gas present in a gas turbine combustion chamber. The method includes tuning a laser to a range containing the absorption lines of species to be analyzed in the gas, and directing the laser light through the combustion chamber and detecting laser light reflected off boundary walls of the combustion chamber. In order to analyze the absorption spectrum measured at high temperatures and pressures, a signature recognition algorithm is applied to the spectrum. The measured absorption spectrum is cross-correlated with a calibration absorption model spectrum for the absorption lines at several temperatures, pressures, and concentrations generated prior to the measurement. Values for pressure, temperature, and concentrations of selected species in the gas are determined simultaneously allowing direct control of the combustion chamber process. An apparatus for carrying out the method is also provided.

11 Claims, 4 Drawing Sheets

(56) References Cited

U.S. PATENT DOCUMENTS

| | | |
|---|---|---|
| 2004/0247522 A1* | 12/2004 | Mills .......................... 423/648.1 |
| 2007/0133921 A1* | 6/2007 | Haffner et al. .................. 385/12 |
| 2008/0289342 A1* | 11/2008 | Sappey et al. ..................... 60/793 |
| 2009/0296776 A1* | 12/2009 | Riza et al. ..................... 374/130 |
| 2010/0128284 A1* | 5/2010 | Riza et al. ..................... 356/519 |
| 2010/0228688 A1* | 9/2010 | Little et al. .................... 705/413 |
| 2010/0292906 A1* | 11/2010 | Girouard et al. ............. 701/100 |
| 2012/0154813 A1* | 6/2012 | Li et al. ......................... 356/437 |

FOREIGN PATENT DOCUMENTS

| | | |
|---|---|---|
| EP | 2093547 A1 | 8/2009 |
| EP | 2107305 A1 | 10/2009 |
| WO | 2007087081 A2 | 8/2007 |
| WO | 2007121032 A2 | 10/2007 |
| WO | 2009052157 A1 | 4/2009 |

\* cited by examiner

METHOD OF ANALYZING AND CONTROLLING A COMBUSTION PROCESS IN A GAS TURBINE AND APPARATUS FOR PERFORMING THE METHOD

FIELD OF INVENTION

The present invention pertains to the field of analyzing and controlling a combustion process in a gas turbine, for example arranged in a power plant for the generation of electrical energy.

BACKGROUND

Control of the combustion process in a combustion chamber of a gas turbine is essential for the performance of a gas turbine and the operating lifetime of its components. A control is furthermore crucial to assure that emissions in the turbine exhaust gases of environmentally harmful gases, as for example $NO_x$, remain within the limitations determined by authorities.

Numerous methods are known for controlling the combustion process and the flame characteristics, as for example the flame temperature and spatial profile, by specific control of the fuel mass flow, temperature, or type, controlled injection of air, or the introduction of water droplets into the combustion chamber.

In order to control the combustion and the flame in the combustion chamber, it is of particular importance to have knowledge of the temperature and pressure within the chamber as well as of the concentrations of water, carbon dioxide, and other gases.

One known method is the use of a thermocouple to determine the temperature and to feed the temperature value into the control loop of the combustion chamber. While this can provide the necessary temperature information, the method is not very suitable for use in gas turbines in the field because the measurement data develop a temperature drift requiring frequent and tedious re-calibrations. Furthermore, the thermocouples, when applied in the high temperature ranges of 1350° C. and above, have a limited operating lifetime and therefore have to be frequently replaced.

Instead of thermocouples, optical sensing methods can be used for the measurement of temperature. These methods mainly include laser absorption spectroscopy, which uses a tunable diode laser source (TDLAS) and transmitting and beam shaping optics that direct the laser light of a certain frequency spectrum through an optically accessible absorbing medium. The tunable laser source is for example a VCSEL or DFB laser, which is tuned over the spectrum encompassing the absorption lines of the components of the medium to be analyzed. Receiving optics and a detector such as a photodiode and a data analysis unit allow determination of not only the temperature, but also concentrations and pressures of a transparent and absorbing medium such as a gas or liquid. Laser absorption spectroscopy is however limited in its applications regarding the pressure of the medium to be measured because at high pressures above 5 bar the absorption lines are broadened, also known as Voigt broadening, which leads to a convolving of the absorption lines and consequent loss of resolution.

WO2009/052157 discloses an apparatus, for performing laser absorption spectroscopy on a gaseous medium, having transmitting and receiving optics, of which at least one is translationally movable. Absorption spectra can thereby be obtained sequentially over a variety of optical paths within the time of movement of the optics. A spectral analysis of the data allows determination of gas type, temperature, and quantity.

EP2107305 discloses sensors sensor placed downstream of the flame in a gas turbine combustion chamber for the measurement of the oxygen concentration. The flame temperature is then determined based on the oxygen concentration value. The oxygen sensor is placed in particular at a location of maximum temperature.

US2008/0289342 describes the difficulty of placing measurement devices in a combustion chamber of a gas turbine due to the harsh environmental conditions, particularly in regard to temperature and pressure. The laser beam of a tunable diode laser is coupled to a fiber and transmitted through the combustion chamber via a port in the outer casing. Optical signals of at least one IR-wavelength are detected and analyzed using a computer to determine the concentration of at least one combustion species. A computer is used to generate engine control input parameters as a function of the concentration of the at least one combustion species. Optical signals of different wavelengths are measured in order to determine the concentration of $H_2O$, CO, or $CO_2$.

SUMMARY

The present disclosure is directed to a method for analyzing and controlling a combustion process in a combustion chamber of a gas turbine by measurement of an absorption spectrum. The method includes providing a molecule absorption spectrum for selected molecules involved in the combustion process using a standard databank for molecule absorption spectra and generating a calibration model absorption spectrum containing absorption lines for selected molecules at a plurality of temperatures, pressures, and concentrations using an algorithm. The method also includes providing one or more tunable laser sources, which are tunable over the spectrum containing absorption lines of species in the combustion chamber. The tunable laser source is tuned to a wavelength range that contains the absorption wavelengths of a selected species in the gas. The method further includes directing the laser light through the gas in the combustion chamber by transmitting optics; detecting the laser light reflected off a boundary wall of the combustion chamber by receiving optics and a detection device; generating a measured absorption spectrum, based on the detected laser light, analyzing the measured absorption spectrum using a signature recognition algorithm by applying a cross-correlation between the calibration model absorption spectrum and the measured absorption spectrum. The method also includes simultaneously deriving from the cross-correlation values for at least one of the following parameters: gas pressure, gas temperature, or concentrations of selected species in the gas, by using the same algorithm as was used for the generation of the calibration model absorption spectrum, and generating control values for the combustion process based on the determined values for gas temperature, gas pressure, and/or species concentration values, and directing the control values to a combustion chamber operation control unit.

In another aspect, the disclosure is directed to an assembly for carrying out the above method. The assembly includes a tunable laser, transmitting optics configured and arranged to transmit the laser light into the combustion chamber of a stationary gas turbine. The assembly also includes receiving optics configured and arranged to receive laser light having passed through the combustion chamber and a signal processing unit that is configured to perform a signature recognition algorithm on measured absorption spectral data and that is operatively connected with a control unit for the gas turbine combustion chamber.

BRIEF DESCRIPTION OF THE FIGURES

The invention is subsequently exemplarily described based on exemplary embodiments with reference to the drawing, without limitation of the general inventive idea. In the drawings.

DETAILED DESCRIPTION OF THE INVENTION
INTRODUCTION TO THE EMBODIMENTS

The present invention is directed to a method of analyzing and controlling the combustion process in a combustion chamber of a gas turbine arranged that allows the measurement of combustion parameters and a control of the combustion process that is improved over those known in the prior art.

According to the invention, a method for analyzing and controlling the combustion process in a combustion chamber of a gas turbine comprises the following steps: prior to the actual measurement during operation of the combustion chamber, providing a molecule absorption spectrum for selected molecules involved in the combustion process using a standard databank for molecule absorption spectra; and generating a calibration model absorption spectrum containing absorption lines for selected molecules at a plurality of temperatures, pressures, and concentrations using an algorithm. For the optical measurement of combustion process parameters, one or more tunable laser sources are provided, which are tunable over the spectrum containing absorption lines of species present or to be expected in the combustion chamber. For the measurement of the combustion parameters themselves, the one or more tunable laser source are tuned to a wavelength range that contains the absorption wavelengths of a selected species in the gas, and the laser light is directed through the gas in the combustion chamber by suitable transmitting optics.

The laser light that is reflected off a boundary wall of the combustion chamber is detected by receiving optics and a detection device. Based on the detected laser light, a measured absorption spectrum is generated, which is analyzed using a signature (or fingerprint) recognition algorithm.

The signature recognition algorithm includes applying a cross-correlation between the calibration model absorption spectrum and the measured absorption spectrum, and simultaneously deriving from the cross-correlation values for one or more of the parameters: gas pressure, gas temperature, and concentrations of selected species in the gas, where the same algorithm is used as was used for the generation of the calibration model absorption spectrum.

Based on the determined gas temperature, gas pressure, and species concentration values, control values for the combustion process are then generated and directed to a combustion chamber operation control unit.

The method and apparatus according to the invention provide a number of advantages for the effective control of the combustion process. The generation of a calibration model absorption spectrum prior to the actual measurement enables a fast simultaneous determination of several combustion parameters. The fast and simultaneous determination of one or more of the parameters pressure, temperature, and concentration of the gaseous media in the combustion chamber allows a control of the combustion process in reaction to the parameter values found within a shorter time frame than methods of the prior art have allowed. Specifically, the method allows a measurement of the combustion parameters in the kHz range, which enables a control of the combustion process that is fast relative to the flame pulsations. Subsequently it allows an improved control of the gas turbine performance. Most importantly, it allows a fast determination of all flame parameters simultaneously, which in turn allows a fast control of the flame temperature and thereby of the gas turbine inlet temperature.

In comparison, a measurement of temperatures in the combustion chamber by a thermocouple allows a control within a time frame of 0.1 seconds or longer.

In addition, the method according to the invention allows a direct measurement of temperature and other parameters directly within the combustion chamber. Compared to control concepts of the prior art this allows a more precise and reliable measurement. For example, in control concepts of the prior art, the temperature measurements are taken within the gas turbine and flame temperatures are deduced from these, where parameters such as cooling and leakage flows have to be taken as unknowns and thereby reduce the precision and reliability of the measurement.

A fast measurement of temperature allows an improved monitoring and control of the flame, its flame temperature, and spatial profile. In particular, the method allows the measurement of temperature changes during flame pulsations, for example between rich and lean flames. Such temperature data allows the controller to limit such pulsations. Pulsations can be controlled more readily by reducing their amplitude and duration such that damages to the combustion chamber due to thermal shocks can be limited. A longer operating lifetime of combustion chamber components such as liner elements as well as the gas turbine blading can thereby be achieved.

Furthermore, combustion events such as the onset of a flame out or flame back can be detected faster, and a control in reaction to such detection can be directed more quickly to the combustion chamber. In particular, the onset of a flame out can be detected quickly and more readily avoided.

Finally and certainly equally important, the method allows via the control of flame temperature and gas species concentrations, an improved control of the emissions in the exhaust gases and their limitations according to the regulations given by the authorities. In particular, in view of the increasing limitations on emissions from fossil fuel combustion, monitoring and effective combustion control is enabled by this method.

The method according to the invention allows the determination of several combustion parameters simultaneously and over the same transmission path through the combustion chamber. This allows an increased precision of the measurement values in that they are determined at precisely the same point in time and in the same spatial range of the flame.

The parameter values therefore contain no temporal or spatial averaging.

The pressure values measured by the proposed method are dependent only on atmospheric pressure changes, which affect the pressure ratio of the compressor. These pressure changes are important in relation to the performance of the gas turbine but they are not controlled.

The application of an algorithm for signature recognition solves the problem of lack of resolution of the absorption lines due to line broadening at high pressures (that is above 5 bars). Specifically, the application of such algorithm allows the precise detection of the absorption lines in spite of the line broadening and in addition allows the simultaneous and fast determination of the parameters. No lengthy iteration processes, which would otherwise slow down the measurement and signal processing, need to be applied.

Because the method according to the invention enables signal processing independent of the pressures and temperatures present in the combustion chamber, the task of measuring combustion parameters at such high pressures and temperatures is reduced to an appropriate positioning of the sensor assembly such that it is not subjected to the high temperatures and pressures of the chamber interior. This is easily solved by known methods involving the use of optical fibers and windows placed in a borescope through the combustion chamber wall. Since the method according to the invention can be performed using only one optical assembly in one place, the effort of positioning the optical assembly is greatly reduced.

Furthermore, the method according to the invention allows a more accurate determination of gas concentrations such as the CO, NO, or $CO_2$ concentration, which can be effectively used for emission control and in subsequent $CO_2$ capture process control within the power plant.

An improved control of the combustion process enabled by the inventive measurement method, also allows an improved control of the lambda-value, which is the air to fuel ratio within the combustion chamber. This in turn further allows improved control of the turbine inlet temperature and gas turbine performance.

A specific embodiment of the analysis and control method according to the invention includes the use of any one of the following algorithms suitable for the signature recognition of a measured spectroscopic data set such as a multivariate algorithm, a fuzzy logic algorithm, wavelet, or neural network algorithm.

A multivariate algorithm includes generating a model absorption spectrum of a species, where a spectrum is generated for each of a multitude of pressure and temperature values. This model absorption spectrum is then cross-correlated with the measured absorption spectrum, and the temperature and pressure values may be determined from the cross-correlation.

In a specific variant of the inventive method comprising cross-correlation, a partial least squares (PLS) regression algorithm is used, where data from the original measured spectrum is projected onto a small number of underlying variables or partial least squares components. The parameter data (such as data for temperature, pressure and concentration) are used in estimating the PLS variables in order to ensure that the first components are the most relevant for predicting the parameter variables.

The described method may be realized by an assembly comprising a tunable laser tunable over a wavelength that includes the absorption lines of interest for the measurement. Furthermore, an assembly comprises transmitting optics configured and arranged to transmit the laser light into the combustion chamber of a gas turbine, receiving optics configured and arranged to receive laser light that has passed through the gas in the combustion chamber, and in particular a signal analysis unit for applying a signature recognition algorithm to measured absorption spectral data using a standard calibration model for absorption lines.

The assembly furthermore comprises a control line for directing control signals from the signal analysis unit to a control unit for the combustion chamber and its lines for fuel and air leading to the combustion chamber.

The method according to the invention can be specifically enabled by the use of a distributed feedback laser (DFB). Such DFB laser is particularly suitable for the method according to the invention because it is operable over a tuning range of about 3 nm that includes the absorption lines typically of interest in a combustion chamber parameter measurement. Specifically, the tuning range includes for example the absorption lines of $H_2O$, $CO_2$ at the wavelengths at 1.392 and 2.004 micrometers, respectively. The tuning range can of course also include the absorption lines of further species present in the gas. In addition, the DFB laser is especially suitable due to the intensity of the laser light it is able to emit for example at 10 mW, which allows a signal intensity at the detection device in the power range of pW to mW following transmittance through the fiber and the chamber, and reflection off a chamber liner. The reflectivity of the thermal barrier coating on the chamber wall liners as they are typically used in gas turbine combustion chambers is sufficiently high. The signal intensity significantly increases the measurement reliability in that it allows the measurement method to be performed without having to apply a special coating to the liners for the purpose of this measurement. It furthermore significantly decreases the maintenance and calibration effort of the measurement assembly.

A DFB-type telecom laser or a Fabry-Perot laser are particularly suitable laser sources for this method due to their intensity and ease of tunability. The laser cavity of the Fabry Perot and distributed feedback lasers can be tuned by electrically varying its temperature and varying the injection current.

The invention may be applied to different types of combustion chambers, including combustion chambers of gas turbines, such as for jet engines and stationary gas turbines for power plants for the generation electrical energy.

An apparatus to perform the method according to the invention includes a tunable laser, a signal generator and laser controller to operate the laser, an optical fiber coupler and fiber arranged to direct the emitted laser light through a combustion chamber wall and through the combustion chamber and receiving optics to receive laser light falling onto the end of the fiber at the combustion chamber wall. The apparatus further includes optical detectors to detect the laser light and devices to direct detected optical signals to a signal processing unit configured to apply a signature recognition algorithm onto the measured signals provided by the fiber. The signal processing includes devices to generate and direct control signals to a combustion chamber control unit. A particular embodiment of the apparatus comprises a tunable DFB laser or Fabry-Perot laser tunable over a range of 3 nm or more.

DETAILED DESCRIPTION

Figure 1:
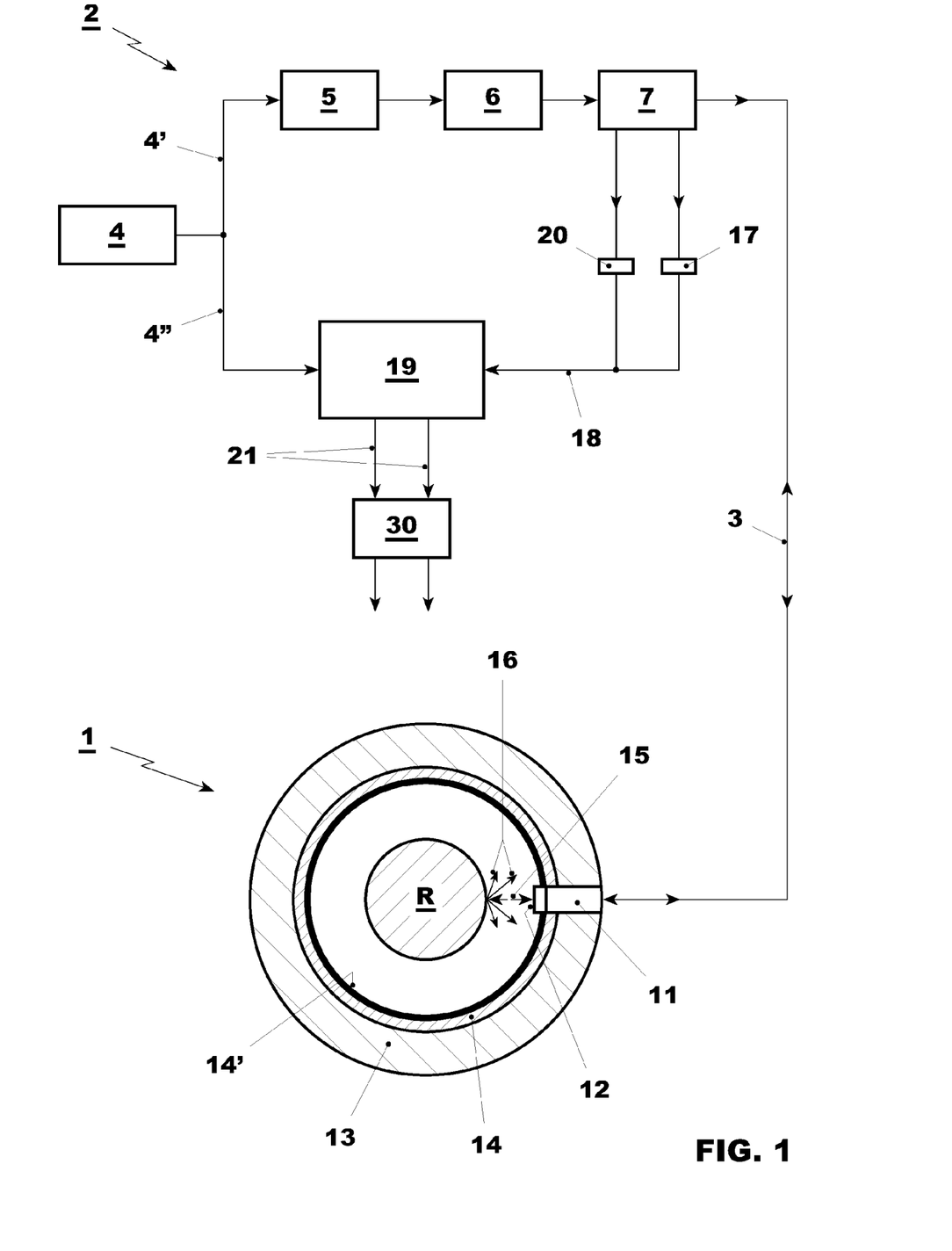
FIG. 1 shows a schematic of an exemplary measurement assembly for performing the measurement and control method according to the invention.

FIG. 1 shows a schematic of a measurement assembly enabling the method according to the invention for analysis and control of a combustion process in a gas turbine. A combustion chamber 1 (shown in cross-section) of a stationary gas turbine is connected to a measurement and analysis system 2 for the measurement of the combustion parameters by absorption spectroscopy. The schematically shown measurement and analysis system 2 comprises as main components a tunable laser system 4, 5, 6, a fiber optic system 3 as transmitting optics, optical detectors 17 and 20, and a line 18 for transmitting signals from both detectors 17 and 20 to a signal analysis unit 19. The system 2, in turn, is connected via an electrical signal line to a control unit 30 for the control of the combustion chamber.

The laser system includes a ramp generator 4 that generates a modulated, electrical drive signal for the laser. The drive signal is for example a saw tooth ramp signal having for example a frequency of 1 kHz or a frequency in the range from 0.5 to 10 kHz. This signal is directed via line 4' to a laser controller 5, which drives a tunable laser 6. The laser 6, for example a distributed feedback laser otherwise used for telecom applications, is tunable over the range of 3 nm.

When taking a set of absorption data over a given spectrum, for example a range of 1 nm is selected that includes several absorption lines. The wavelength range can be chosen such that the strongest absorption lines are included. A wavelength range as wide as 1 nm or more and the application of the signature recognition algorithm enables the pressure broadening to be overcome.

The DFB laser is controlled to emit over this range of wavelengths, for which the laser cavity size is varied by a controlled variation of its cavity length by a controlled variation of the cavity's temperature as well as by control of its injection current.

The DFB laser 7 is coupled to a fiber optic system 3, which includes a fiber circulator or fiber coupler and an optical fiber connected to a borescope 11. The borescope is arranged in the combustion chamber casing 13 and chamber liner 14 with thermal barrier coating 14'. The fiber end is for example suitably equipped with sapphire optics, which are able to withstand the high temperatures of an operating gas turbine combustion chamber.

The sapphire optics are arranged and aligned with the optical fiber to direct the pulsed laser along a given preselected optical path through a section of the combustion chamber containing the gas to be analyzed. The DFB laser 7 emits modulated light intensity, of which some light is directed to a reference detector 17, which monitors the output intensity. The rest of its output is coupled by a fiber optic circulator or other coupler into an optical fiber 3. The fiber directs the laser light through a borescope and through a sapphire optical element at the end of the fiber, which also acts as a window to the combustion chamber. The laser light is thereby transmitted along optical path 15 through the interior of chamber 1 and directed to the opposite chamber wall. Some laser light beams 16 reflected off the liner's thermal barrier coating 14' are received by said sapphire optics, and transmitted by the optical fiber 3 to a detector 20. Both detectors 17 and 20 convert their detected optical signals into an electrical signal, which are directed via line 18 to a signal analysis unit 19 able to perform the signature recognition of the measured absorption spectrum. A sufficient intensity at the detector 20 is assured due to the high intensity put out by the DFB laser. No mirrors must be placed or specifically aligned on the combustion chamber wall, and the fiber and integrated sapphire receiving optics, once placed in a borescope or similarly suitable passage through the combustion chamber wall, need not to be specifically aligned. A reflection off any part of the combustion chamber wall will allow detection of a return signal sufficiently strong enabling the signal processing according to this invention.

Unit 19 is configured to receive the electrical signals from the two detectors 17 and 20 and to perform the signal analysis according to the signature recognition algorithm of the invention. It is also configured to receive a further electrical reference signal from the signal generator 4 via line 4'. Unit 19 is connected to control lines 21, which direct generated control signals to an operation control unit 30 of the combustion chamber.

Figure 2:
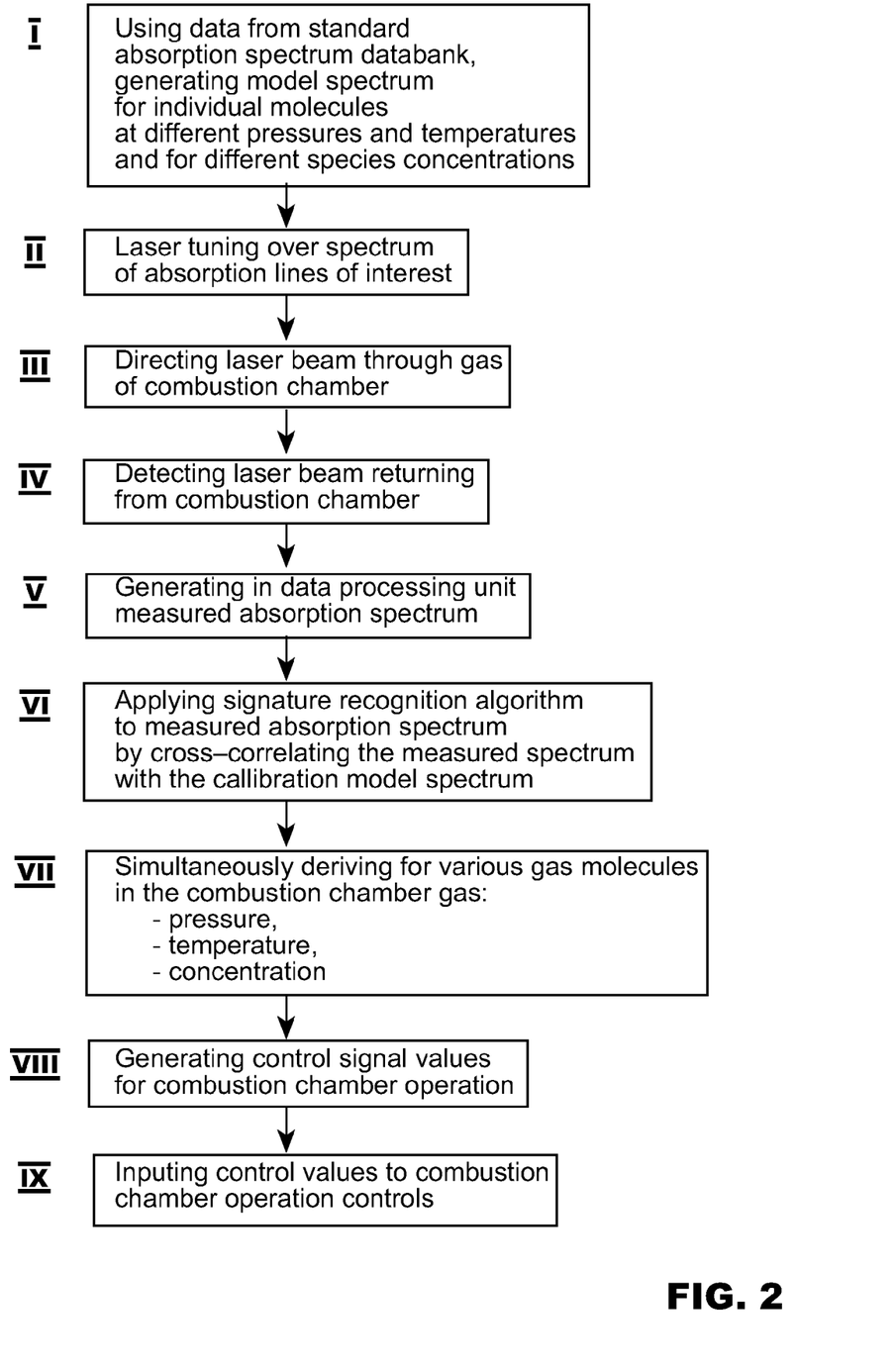
FIG. 2 shows a flow-chart of the method of measurement and control of a gas turbine combustion chamber.

The analysis and control method according to the invention will be described as follows in detail on basis of the flowchart shown in FIG. 2.

In step I, prior to the actual absorption spectrum measurement in the gas turbine combustion chamber, a calibration model absorption spectrum is generated using a standard molecule absorption spectrum for selected molecules expected to be present in the chamber. For this, a standard databank for molecule absorption spectra is used such as HITRAN. Other possible databanks are, for example, GEISA or HITEMP. For a number of temperatures in the range of 500-1800° C. and pressures in the range 1-35 bar as well as for several concentrations of species as they are likely to occur in the gas, a calibration model absorption spectrum is generated. For this an algorithm is used, for example a multivariate algorithm. The same algorithm will again be used in the cross-correlation later, which enables the direct and simultaneous determination of the temperatures, pressures, and concentrations. Due to the prior determination of the calibration model spectrum, a fast and simultaneous determination of the gas parameters is made possible.

Figure 4:
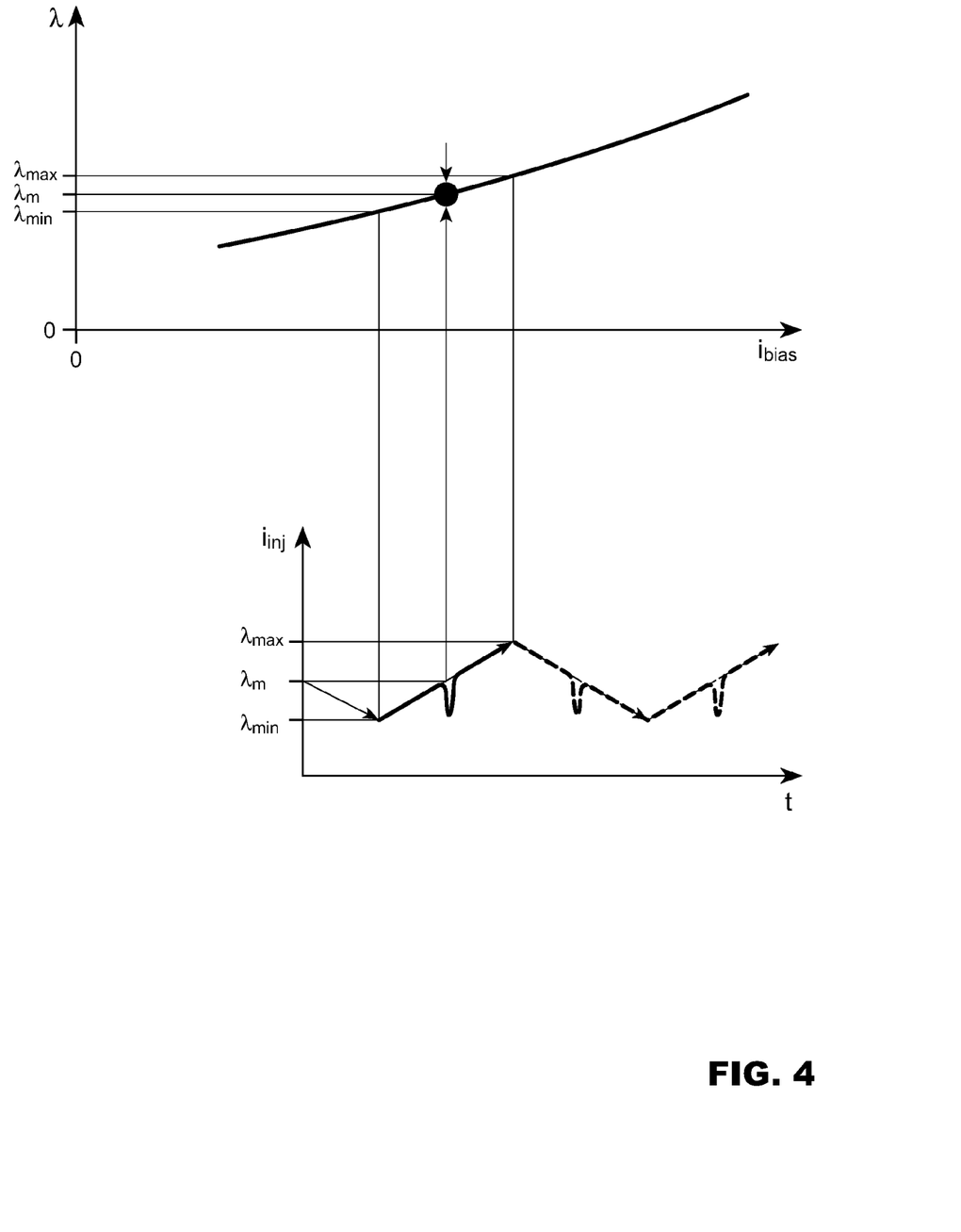
FIG. 4 shows curves illustrating the laser control over a given tuning range used in the inventive method.

In step II of the method, the laser, for example a DFB laser, is tuned over a selected wavelength spectrum. The laser is first tuned as shown in the top curve of FIG. 4 to a selected first wavelength $\lambda_m$ by tuning the laser cavity by cavity temperature control and a variation of the bias current $i_{bias}$. The temperature control is comparatively slow, whereas the variation of the bias current can occur faster. In addition, the laser is fine-tuned by variation of the laser injection current as shown in the lower curve in FIG. 4. The signal generator 4 is operated to generate a modulated triangle injection current signal $i_{inj}$ as shown in FIG. 4 according to a ramp function for the injection current $i_{inj}$, which generates a tuning about the center wavelength $\lambda_m$ over a range between a minimum and maximum wavelength ($\lambda_{min}$ and $\lambda_{max}$). The modulation frequency of the laser injection current can be in the kHz range, for example between 1 and 10 kHz.

In step III of the method, the emitted laser light is directed by the fiber coupler and optical fiber to the combustion chamber and via the borescope and sapphire optics at the end of the fiber into the interior of the chamber. The sapphire receiving optics and fiber allows the return light from the chamber to be directed to a detector (step IV).

The electrical signal generated by detector 20 for the return laser light is processed in processing unit 19 together with the electrical signal generated by detector 17 for the reference laser intensity and the ramp signal directed via line 4" from the ramp generator 4. In step V, unit 19 generates with these three signals a measured absorption spectrum for the given wavelength range.

The ramp signal as shown in FIG. 4 is repeated in order to allow several spectral scans and a continuous sampling of the absorption lines over time. An absorption spectrum as generated by unit 19 is shown for example in curve A or B of FIG. 3. These spectra have broadened absorption lines due to the high temperature and pressures relative to ambient. An absorption spectrum without the broadening effects as it would be measured at ambient conditions is shown in curve C.

Figure 3:
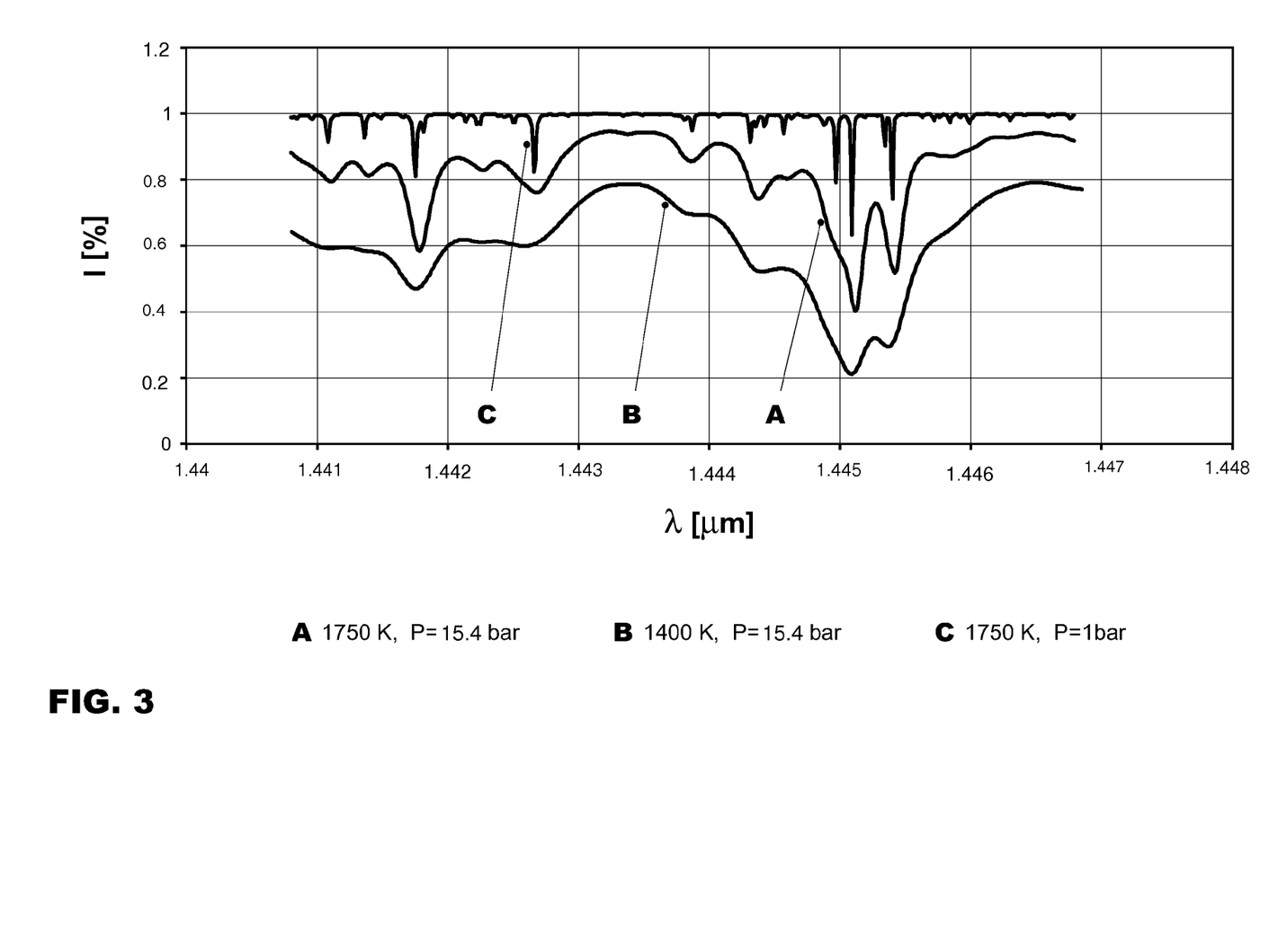
FIG. 3 shows exemplary spectra according to the return signal from a combustion chamber and normalized according to the measured reference laser intensity and an exemplary spectrum following signal processing according to the inventive method using a multivariate algorithm.

A precise and unambiguous determination of the absorption lines is not possible from such a spectrum with broadened absorption lines as in curves A or B.

According to step VI, the measured absorption spectrum is processed using the signature recognition algorithm according to the invention. Unit 19 provides a molecule absorption spectrum for given molecules, which is based on standard absorption spectral data as provided by the HITRAN (HIgh resolution TRANsmission) database recognized as international standard, whereas other similar databanks may also be used. It furthermore provides a calibration model spectrum generated for the selected molecules using the standard spectral data and calculating the spectrum for different combinations of temperature, pressure, and concentration values.

In steps VI, the calibration model spectrum is cross-correlated with the measured absorption spectrum. By comparison of the measured spectrum to the model calibration spectra, the temperature, pressure, and concentration of the species in the gas having the absorption line at $\lambda_m$, can be determined.

The cross-correlation between the measured and the calibration absorption spectrum yields values that are used to derive in step VII the gas pressure, gas temperature, and/or the species concentrations. Because the same algorithm is used for deriving these gas parameters as was used for generating the calibration model absorption spectrum for a variety of these parameters, all these parameters can be determined simultaneously by one calculation.

The problem of signal distortion due to high temperatures and pressures is solved by the inventive signature recognition algorithm applied to this type of spectrum.

All these parameters can be simultaneously determined at a frequency rate in the kHz range allowing analysis of the combustion process and flame quality at this same rate.

In step VIII, the gas parameters determined in unit 19 are directed to combustion chamber control unit 30, which generates combustion chamber control signals (step VIII). In Step IX, unit 30 directs the control signals to the various combustion chamber operation actuators including one or more of a control of airflow, inlet guide vane positions, and fuel mass flow. In a further embodiment of the method, several lasers are used instead of only one, for example three to six DFB lasers. Each laser is tuned to a different wavelength range thereby increasing the total wavelength range covered in the absorption measurement. In order to distinguish the individual laser signals, the lasers are intensity modulated by different ramp signals, where none of the modulation frequencies are a whole number multiple of another frequency. The lasers and optical detectors for the laser reference signals and return signals from the combustion chamber are connected so to allow optical or electronic heterodyne detection. The resulting absorption spectrum is processed in same manner using signature algorithms as described above.

Such measurement with several laser sources enables a measurement over a larger wavelength range and as such over a greater number of absorption lines and also measurement over ranges having no absorption lines that can serve as reference measurements. The larger data samples thereby achieved allow an increased measurement reliability and precision.

TERMS USED IN THE FIGURES

1 gas turbine combustion chamber
2 absorption spectrum measurement system
3 optical fiber
4 signal generator
4' signal line
4' signal line
5 laser controller
6 tunable laser
7 fiber coupler
11 borescope
12 sapphire optics
13 combustion chamber wall
14 chamber liner
14' thermal barrier coating
15 optical path
16 reflected light
17 detector
18 optical signal line
20 reference detector
19 signal analysis unit
21 electrical control signal line
30 combustion chamber control unit
I-X steps of flow chart
A absorption spectrum at first pressure and temperature
B absorption spectrum at second pressure and temperature
C absorption spectrum at ambient (room) pressure and temperature

What is claimed is:

1. A method for analyzing and controlling a combustion process in a combustion chamber of a gas turbine by measurement of an absorption spectrum, the method comprising:
   providing a molecule absorption spectrum including a range of absorption lines for selected molecules of gas involved in the combustion process in the combustion chamber by using a databank containing standards for molecule absorption spectra including the selected molecules of the gas, and generating a calibration model absorption spectrum containing absorption lines for the selected molecules of the gas at a plurality of temperatures, pressures, and concentrations of the selected molecules of the gas using an algorithm;
   providing one or more tunable laser sources, which are tunable over the spectrum containing absorption lines of a selected species of the gas in the combustion chamber;
   tuning the one or more tunable laser sources to a wavelength range that contains absorption wavelengths of the selected species in the gas;
   directing laser light from the one or more tunable laser sources through the gas in the combustion chamber via transmitting optics;
   detecting the laser light reflected off a boundary wall of the combustion chamber via receiving optics and a detection device;
   generating a measured absorption spectrum for the selected species of the gas in the chamber, based on the detected laser light;
   analyzing the measured absorption spectrum using a signature recognition algorithm by applying a cross-correlation between the calibration model absorption spectrum and the measured absorption spectrum;
   deriving, simultaneously, from the cross-correlation, values for a gas temperature of the selected molecules of the gas in the chamber by using the same algorithm as was used for the generation of the calibration model absorption spectrum;
   generating control values for the combustion process based on the derived values for the gas temperature, and directing the control values to a combustion chamber operation control unit; and
   controlling the combustion process using the generated control values.

2. The method according to claim 1, further comprising: using for the signature recognition algorithm a multivariate algorithm.

3. The method according to claim 2, wherein the multivariate algorithm includes a partial least squares regression algorithm.

4. The method according to claim 1, further comprising: using for the signature recognition algorithm one of a wavelet algorithm and a fuzzy logic algorithm.

5. The method according to claim 1, further comprising: using for the signature recognition algorithm a neural network algorithm.

6. The method according to claim 1, further comprising: using a distributed feedback (DFB) laser as the one or more tunable laser sources.

7. The method according to claim 6, further comprising: modulating the DFB laser at a frequency in the range from 0.5-10 kHz.

8. The method according to claim 6, further comprising: modulating the DFB laser at a frequency in the kHz range.

9. The method according to claim 6, further comprising: tuning the DFB laser back and forth over a given wavelength range by modulating a laser injection current according to a triangular function to tune the DFB laser over the given wavelength range.

10. The method according to claim 1, further comprising: tuning each of the tunable lasers to a respectively different wavelength range; modulating each laser at a different frequency, directing their emitted light through transmitting optics through the combustion chamber; detecting the laser light reflected off a combustion chamber wall by heterodyne detection; and analyzing the measured absorption spectrum using the signature recognition algorithm.

11. The method according to claim 1, further comprising: deriving, simultaneously, from the cross-correlation, values for the gas pressure, or concentrations of the selected species in the gas, by using the same algorithm as was used for the generation of the calibration model absorption spectrum.

* * * * *